(12) United States Patent
Schwartz

(10) Patent No.: US 8,905,756 B2
(45) Date of Patent: Dec. 9, 2014

(54) THERMOFORMED DENTAL APPLIANCE FROM MULTIPLE PLY SHEET

(75) Inventor: Dann Schwartz, Kenner, LA (US)

(73) Assignee: Dentsply International Inc., York, PA (US)

( * ) Notice: Subject to any disclaimer, the term of this patent is extended or adjusted under 35 U.S.C. 154(b) by 0 days.

(21) Appl. No.: 11/895,133

(22) Filed: Aug. 23, 2007

(65) Prior Publication Data

US 2009/0298006 A1  Dec. 3, 2009

Related U.S. Application Data

(60) Provisional application No. 60/823,278, filed on Aug. 23, 2006.

(51) Int. Cl.
| | | |
|---|---|---|
| *A61C 3/00* | (2006.01) | |
| *A61C 15/00* | (2006.01) | |
| *A61C 9/00* | (2006.01) | |
| *A61C 5/00* | (2006.01) | |
| *A61C 5/14* | (2006.01) | |
| *A61C 7/08* | (2006.01) | |

(52) U.S. Cl.
CPC ..................................... *A61C 7/08* (2013.01)
USPC .............. 433/24; 433/34; 433/215; 433/216; 128/861; 128/862

(58) Field of Classification Search
USPC .............. 433/215–225, 24, 80, 81, 89, 5–12, 433/34–37, 215–21; 128/859–862
See application file for complete search history.

(56) References Cited

U.S. PATENT DOCUMENTS

| | | |
|---|---|---|
| 6,454,565 B2 | 9/2002 | Phan |
| 6,524,101 B1 | 2/2003 | Phan |
| 6,964,564 B2 | 11/2005 | Phan |
| 2002/0142258 A1* | 10/2002 | Chishti et al. ..................... 433/6 |
| 2002/0187451 A1* | 12/2002 | Phan et al. ......................... 433/6 |
| 2004/0234929 A1* | 11/2004 | Fischer et al. ................ 433/215 |
| 2005/0100853 A1* | 5/2005 | Tadros et al. ..................... 433/6 |
| 2006/0008760 A1* | 1/2006 | Phan et al. ......................... 433/6 |
| 2006/0216670 A1* | 9/2006 | Leichtung ..................... 433/167 |
| 2007/0087300 A1 | 4/2007 | Willison et al. |

* cited by examiner

*Primary Examiner* — Yogesh Patel

(74) *Attorney, Agent, or Firm* — McNees Wallace & Nurick LLC

(57) ABSTRACT

A dental appliance comprising at least two plies of thermoformable material, wherein a first ply of a first material, having a first set of characteristics properties, provides a first primary surface of the dental appliance and wherein a second ply of a material different from the first ply, having a second set of characteristic properties, provides an opposing second primary surface of the dental appliance.

2 Claims, 2 Drawing Sheets

THERMOFORMED DENTAL APPLIANCE FROM MULTIPLE PLY SHEET

The present invention is generally directed to dental appliances and more particularly to thermoformed dental appliances.

BACKGROUND

Orthodontic and other dental laboratories provide services for the custom-fabrication of dental appliances for an individual patient according to a treatment plan and a prescription provided by an attending orthodontist or dentist. A poured and cured stone replica of a patient's mouth structure, such as an initial malocclusion for example, is typically provided by the doctor for the laboratory's use.

The dental technicians at the lab first modify the stone model by cutting the mal-positioned teeth free of the model and the adjacent teeth. Next, a technician repositions the teeth on the model semi-rigidly into desired, ideal positions as specified by the doctor and as determined by the doctor's diagnosis and subsequent treatment plan. After the stone model has been modified or "corrected" in this manner, the model will be positioned within an appliance-forming machine where a sheet of thermo-formable elastomeric material is typically "sucked-down" or pressed over the stone model(s).

The use of thin sheets of various thermo-formable plastics including vinyl and olefin-type materials has been adopted for many current appliances. This, along with an efficient forming process involving the rapid use of pressure, vacuum and heat, has replaced prior molding and casting processes. The use of these materials, including polypropylene in sheet form and in thicknesses of about 1 mm (before thermoforming), eliminates the time-consuming steps of mixing, catalyzing and curing and optionally heat-curing in a pressure flask, as was required by natural rubber, medical-grade urethane, silicone and vinyl silicone series materials.

Polypropylene (PP), for example, is often used in making dental appliances because it is non-reactive chemically and thoroughly biocompatible. However, PP alone may exhibit plastic creep over time, resulting in minor, but undesirable changes in the appliance's shape and it may also lack the level of clarity desired by some patients. Likewise, PP's characteristics for making a dental appliance by thermoforming is adequate, but not ideal for consistent, accurate products. This may prevent cost effective production of consistent, high-quality appliances demanded by dentists and their patients.

Better thermoforming characteristics are found in medical grade copolyester sheets, which are also used to make dental appliances. However, dental appliances made from copolyester sheets alone have a tendency to become brittle over time. As a result, a patient wearing such an appliance who has a tendency to grind his teeth may grind into or through the appliance, reducing or eliminating the appliance's effectiveness.

SUMMARY OF THE INVENTION

It has been discovered that a multiple ply sheet of different materials can be used to manufacture a dental appliance that has the desired mechanical properties for a dental appliance while also exhibiting the type of thermo-forming characteristics that permit dental appliances to be consistently produced with high quality.

According to an exemplary embodiment of the invention, a dental appliance comprises a thermoformable material having at least two plies, in which each of the two plies are of different materials. The material of the first ply has a first set of characteristic properties and forms a first surface of the appliance and the material of the second ply has a second set of characteristic properties and forms an opposing second surface of the appliance. Each ply has two major surfaces; the first and second plies have a common interface, with one ply having a major surface facing away from the teeth and the other ply having a major surface facing toward the teeth.

According to another exemplary embodiment of the invention, a method of making a dental appliance is also provided. The method includes providing a sheet of thermoplastic material having at least two plies as described above, preferably by co-extruding, and thereafter thermoforming the sheet to form a dental appliance.

One advantage of exemplary embodiments of the invention include providing a thermoformed dental appliance made from a multi-ply sheet of different materials that has better combined mechanical and thermoforming properties than a sheet of a single material.

Another advantage of certain exemplary embodiments of the invention is that the thickness of the multi-ply sheet used in the dental appliance is comparable with that of single ply materials used in thermoformed dental appliances.

DETAILED DESCRIPTION OF EXEMPLARY EMBODIMENTS

Figure 1:
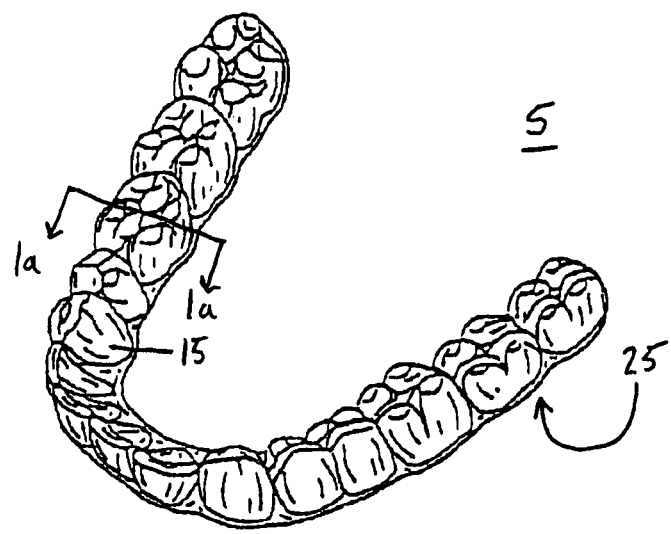
FIG. 1 illustrates a dental appliance according to one exemplary embodiment of the invention.

As used herein, "dental appliance" means any device capable of being formed for use in dental applications with or without additional components such as wires and includes, by way of example only, aligners, positioners, night guards, retainers, splints, bleaching trays, and anterior bridges. FIG. 1 illustrates an exemplary dental appliance 5 according to one embodiment of the invention. The appliance 5 has a first, or outer, surface 15 that, when worn, is exposed to the patient's mouth tissue, as well as any food or drink entering the patient's mouth. A second, inner surface 25 of the dental appliance 5 that is arranged to face the surface of one or more of the patient's teeth.

Figure 2:
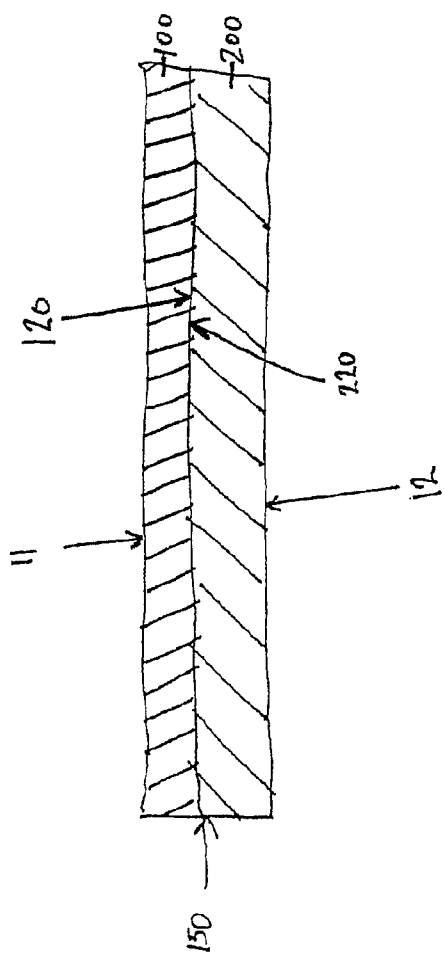
FIG. 2 illustrates a coextruded sheet for use in forming a dental appliance according to an exemplary embodiment of the invention.

The appliance 5 is formed from a multi-ply sheet 10 as shown in FIG. 2. The sheet 10 includes a first ply 100 of a first material and a second ply 200 of a second material different from the first material. The sheet 10 has a first surface 11 that is also a first surface of the first ply 100 and an opposing second surface 12 that is also a first surface of the second ply 200. The first surface 11 of the sheet 10 may be positioned during the dental appliance manufacturing process to form either one of the outer surface 15 or the inner surface 25 of the dental appliance 5, such that the sheet's opposing second surface 12 forms the opposite surface 25 of the dental appliance 5.

The first ply 100 in the multi-ply sheet 10 can be any thermoplastic or elastomeric material that is permanently deformable under heat or pressure and that has properties suitable for use in a dental appliance. Thermosetting materials may also be used, which, for example, may be cured during the thermoforming process. By "permanently deformable" is meant that the materials can be formed to a desired shape under conditions of elevated pressure and/or temperature and which will substantially retain that shape under normal conditions experienced in the mouth, but does not necessarily mean that subjecting the materials to elevated pressures and temperatures would not cause permanent deformation to a new, different shape. Properties which are desirable for use in a dental appliance include transparency, toughness, and biocompatibility by way of example only. Copolyesters have the characteristic of providing consistently accurate thermoformed dental appliances and may be particularly suitable materials for use as the first ply 100. Other exemplary materials for use as the first ply 100 include ethyl vinyl acetate (EVA), polypropylene (PP), polyvinylchloride (PVC), low density polyethylene (LDPE), and high density polyethylene (HDPE).

The second ply 200 in the multi-ply sheet 10 can be any thermoplastic or elastomeric material permanently deformable under heat or pressure that is a different composition from the first ply material. The second ply material should also have suitable properties for use in a dental appliance and should have a coefficient of thermal expansion comparable or equal to that of the first ply material. Otherwise, the subsequent thermoforming process to make the dental appliance 5 may cause one ply to shrink disproportionately with respect to the other, which may result in undesirable crimping or puckering that could lead to a poor quality or unusable dental appliance. One suitable material for the second ply 200 include copolyester ethers, although copolyesters of a composition different from the first ply material may also be used. Other exemplary materials for use as the second ply 200 include ethyl vinyl acetate (EVA), polypropylene (PP), polyvinylchloride (PVC), low density polyethylene (LDPE), and high density polyethylene (HDPE), and may also include blends of polymeric materials, with or without a rubberizing additive.

Because certain copolyesters may have excellent thermoforming properties but less desirable mechanical characteristics, the material selected for the second ply 200 may be selected for mechanical properties to provide a multi-ply sheet 10 having a combination of desirable properties. Conversely, if the material selected for the second ply 200 has good mechanical properties, it may, but does not necessarily need to have comparably good thermoforming properties if the material for the first ply 100 is selected for that characteristic.

In the preferred embodiments in which the multiple ply sheet 10 is manufactured by coextrusion, the materials of the two plies 100, 200 should also be compatible with one another for the coextrusion operation or be capable of being made compatible through the addition of a compatibility agent as are known to those of ordinary skill in the art.

Because the sheet 10 is multi-layered and because the plies 100, 200 may have different characteristic properties, the materials selected for each ply 100, 200 may be selected depending on whether the particular ply will primarily be in contact with the tooth surface, i.e. the ply providing the inner surface 25 of the dental appliance 5, versus the ply primarily in contact the soft tissue of mouth, i.e. the ply providing the outer surface 15 of the dental appliance 5. It will be appreciated that the different materials may be of different polymeric classes (e.g., copolyesters versus copolyester ethers) or may be of the same class, but have different compositions (e.g., copolyester A versus copolyester B).

According to a presently preferred embodiment, the sheet 10 is a copolyester/copolyester ether coextruded sheet and more specifically is a coextruded sheet having plies of Medstar and Ecdel. "Medstar" is a trade designation for a copolyester commercially available from Eastman Chemical Co. of Kingsport, Tenn. "Ecdel" is a trade designation for a copolymer of cyclohexane dicarboxylic acid, ethylene glycol, and cyclohexane-1,4-dimethanol that is also commercially available from Eastman Chemical.

In accordance with the presently preferred embodiment, the multi-ply sheet 10 is produced by coextrusion, although chemical and/or mechanical bonding techniques may also be used to form the multi-ply sheet 10, such as using adhesive, surface tension, a joining element, or by imparting a surface finish, such as a dovetail, that permits one ply to capture another, by way of example only.

Techniques for coextruding sheets of two or more plies of different material is well known to those of ordinary skill in the art. In accordance with exemplary embodiments of the invention, the die(s) for use in the coextrusion process is sized and dimensioned to produce a multi-ply sheet 10 having a total thickness (before thermoforming) of about 0.25 mm to about 5 mm, more preferably less than about 1 mm and still more preferably less than about 0.875 mm. Each ply within the multi-ply sheet is typically equal in thickness, although the relative thicknesses can be varied, and may be as high as about 70% to about 90% of one and about 10% to about 30% of the other.

Referring to FIG. 2, an opposing second surface 120 of the first ply 100 is positioned to face toward an opposing second surface 220 of the second ply 200. It will be appreciated that the sheet 10 may be extruded such that the plies 100, 200 are in direct contact with one another at an interface 150. Alternatively, a binder or adhesive may be intermediate the two plies 100, 200 to chemically or mechanically enhance the plies' adherence to one another to produce a single sheet 10.

It will further be appreciated that more than two plies can be employed, although the overall sheet thickness should remain as described above. The material selected for any subsequent ply can be the same or different than the material used in any other ply, although at least one ply of a different material is typically intermediate any two plies of the same material. In some embodiments, it may even be possible to use an intermediate ply of a material, as for example, a bonding layer, that is not biocompatible but which has particularly desirable other characteristics that is sandwiched between two outer plies of materials which are biocompatible, thereby negating the bio-incompatibility of the intermediate material.

Once the multiple ply sheet 10 has been produced, it may be used in dental appliance 5 manufacture such as by thermoforming it to a final shape in a manner known to those of ordinary skill in the art. Generally, thermoforming is accomplished by subjecting the multiple ply sheet 10 to a combination of pressure, heat and/or vacuum while positioned over a stone model which results in the sheet 10 generally conforming to the shape of the model to form the dental appliance 5. Custom appliances are created by providing a model of a particular patient's mouth in which the dental appliance will be used; the stone model may be a model of the patient's actual mouth or, in the case of an aligner, for example, the stone model may be a slightly modified version of the patient's mouth created by a laboratory technician to which the actual mouth is expected to conform over time.

Figure 1A:
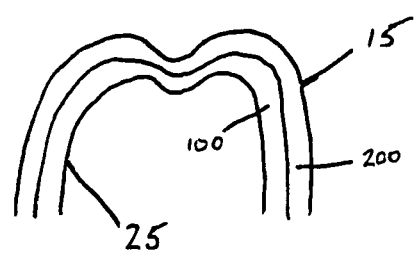
FIG. 1a is a cross-sectional view of the dental appliance of FIG. 1.

Because the multi-ply sheet 10 will typically have two surfaces 11, 12 with different characteristics from one another, when the sheet 10 is aligned with the stone in preparation for thermoforming, the ply to be primarily in contact with the teeth should be arranged to face the stone so that it forms the inner surface 25 of the dental appliance 5. That is, whether the first surface 11 of the multi-ply sheet 10 (i.e., the outer surface 110 of the first ply 100) corresponds to the outer surface 15 or the inner surface 25 of the dental appliance 5 depends on whether the material selected for the first ply 100 is better suited for facing toward or away from the surface of the patient's tooth. For example, in accordance with the preferred embodiment illustrated in FIG. 1a in which the multiple ply sheet 10 has a first ply 100 of Medstar and a second ply 200 of Ecdel, the sheet 10 is positioned and the manufacturing process is conducted so that the Medstar material (i.e., the first ply 100) forms the inner surface 25 of the dental appliance 5, while the Ecdel material (i.e., the second ply 200) forms the outer surface 15 of the dental appliance 5.

In some cases, it may be economical to produce the multi-ply sheet 10 in dimensions larger than would ordinarily be used for making any single dental appliance 5. Thus, the multi-ply sheet 10 may be provided in large rolls or sheet form which can be cut into smaller pieces by a laboratory technician. Alternatively, the multi-ply sheet 10 may be cut down into individual sized pieces as part of the manufacturing and packaging process for use in one or more specific models of thermoforming devices. To keep the smaller multi-ply sheets 10 from sticking together and prevent damage during handling, a protective film may be removably adhered to each surface 11, 12 of the sheet 10.

While the foregoing specification illustrates and describes exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A thermoformed dental appliance comprising
at least two plies of thermoformable material, wherein a first ply comprising a copolyester material, having a first set of characteristic properties, provides a first primary surface of the dental appliance and wherein a second ply comprising a copolyester ether material different from the first ply, having a second set of characteristic properties, provides an opposing second primary surface of the dental appliance, wherein the first ply and the second ply have a combined thickness before thermoforming of from 0.25 to 5 mm;
wherein the first ply comprises a copolymer of deformable thermoplastic or elastomeric material having properties suitable for use in a dental appliance, the deformable thermoplastic or elastomeric material comprising one of: ethyl vinyl acetate, polypropylene, polyvinylchloride, low density polyethylene, or high density polyethylene, and;
wherein the copolyester ether material comprises cyclohexane dicarboxylic acid, ethylene glycol and cyclohexane-1,4-dimethanol; and
the dental appliance having teeth receiving cavities conforming to a shape of a patient's mouth or a modification of the patient's mouth based on a stone model, wherein the first primary surface comprises an inner surface arranged to be in contact with a patient's teeth, that forms the inner surface of the dental appliance, and wherein the second primary surface forms an outer surface towards the patient's mouth tissue, and the first ply and the second ply are joined at a common interface.

2. The thermoformed dental appliance of claim 1, wherein the dental appliance is formed from a multi-ply sheet, wherein the multi-ply sheet is comprised of the first ply and the second ply.

* * * * *